United States Patent [19]

Ansmann

[11] Patent Number: 4,735,742
[45] Date of Patent: Apr. 5, 1988

[54] PALMITATE-STEARATE O/W EMULSIONS AND THEIR PREPARATION

[75] Inventor: Achim Ansmann, Hilden, Fed. Rep. of Germany

[73] Assignee: Henkel Kommanditgesellschaft auf Aktien, Duesseldorf, Fed. Rep. of Germany

[21] Appl. No.: 904,534

[22] Filed: Sep. 5, 1986

[30] Foreign Application Priority Data

Sep. 7, 1985 [DE] Fed. Rep. of Germany ....... 3531971

[51] Int. Cl.⁴ .............................................. B01J 13/00
[52] U.S. Cl. .................................... 252/312; 252/314; 426/602; 514/943
[58] Field of Search ................. 252/312, 314; 514/943

[56] References Cited

U.S. PATENT DOCUMENTS

| | | | |
|---|---|---|---|
| 1,930,845 | 10/1933 | Ulrich et al. | 252/312 |
| 2,207,256 | 7/1940 | Kapp | 252/1 |
| 2,573,599 | 10/1951 | Price | 252/312 |
| 2,684,949 | 7/1954 | McMillan et al. | 252/314 |
| 2,798,053 | 7/1957 | Brown | 260/2.2 |
| 4,234,450 | 11/1980 | Hirayama et al. | 252/312 X |

FOREIGN PATENT DOCUMENTS

| | | |
|---|---|---|
| 775080 | 1/1968 | Canada ................. 252/312 |
| 0111895 | 6/1984 | European Pat. Off. . |
| 1948800 | 1/1971 | Fed. Rep. of Germany . |
| 907881 | 3/1946 | France . |
| 145602 | 2/1921 | United Kingdom . |
| 780801 | 8/1957 | United Kingdom . |

OTHER PUBLICATIONS

Ansmann, "Fette Seifen Anstrichmittel", vol. 87, No. 10 (Oct. 85) pp. 408–410.
"Journal of Organic Chemistry", vol. X, Williams & Wilkins Co. (pub.) Baltimore, 1945, pp. 170–174.
Ploog, "Seifen, Ole, Fette, Wachse", vol. 109, No. 8 (May, 83) pp. 225–229.
Tillotson (J. Soc. Cosmet. Chem. 6, (1955) pp. 40–49.

Primary Examiner—Richard D. Lovering
Attorney, Agent, or Firm—Ernest G. Szoke; Henry E. Millson, Jr.; Mark A. Greenfield

[57] ABSTRACT

An oil-in-water emulsion and method for forming same, containing as the primary emulsifier, a palmitic acid soap and a stearic acid soap, in a palmitic:stearic weight ratio of 1:025–0.67.

15 Claims, 1 Drawing Sheet

PALMITATE-STEARATE O/W EMULSIONS AND THEIR PREPARATION

BACKGROUND OF THE INVENTION

1. Field of the Invention

This invention relates to oil-in-water (O/W) emulsifiers comprising palmitate-stearate compositions, methods of emulsifying, and the resultant emulsions.

2. Statement of Related Art

The stability, fineness and rheological behavior of O/W-emulsions are critically determined by the type and composition of the emulsifier. Among the emulsifiers used for the preparation of O/W-emulsions, fatty acid soaps are particularly important because of their high emulsifying power for all the usual liquid and semisolid oil and fat components, and because of their easy availability. Among the fatty acid soaps, the most suitable by virtue of their hydrophilicity are the soaps of technical stearic acids. In the cosmetics field, these stearate-based emulsions are also known as stearate creams.

The technical stearic acids most widely used as base materials for emulsifiers are mixtures of stearic acid and palmitic acid which are obained by the saponification of tallow and separation of the solid fatty acid fraction, known as "stearin". The "triple-pressed" stearins obtained in this way consist of 50 to 55% by weight palmitic acid, 40 to 45% by weight stearic acid and small amounts of myristic acid, pentadecanoic acid, heptadecanoic acid and oleic acid. Another grade of technical stearin is obtained by hardening, (i.e. by hydrogenation of the unsaturated fractions of tallow fatty acid). A stearin obtained in this way comprises 25 to 30% by weight palmitic acid, 60 to 65% by weight stearic acid and small amounts of myristic acid, pentadecanoic acid, heptadecanoic acid, oleic acid and arachic acid.

Although investigations have been conducted into the influence of the $C_{16}/C_{18}$-ratio of stearic acid/palmitic acid mixtures on the crystallization behavior and the physical-chemical properties of such mixtures, for example by Tillotson (J. SOC. COSMET. CHEM. 6, (1955), Pp. 40–49), nothing is known of the influence of the carbon-chain distribution of these fatty acids on the emulsifying power of the soaps obtainable therefrom.

O/W-emulsions are metastable systems consisting of a discontinuous (inner) oil phase and a continuous (outer) aqueous phase which are for a finite period of time stabilized by the interface-stabilizing effect of the emulsifier. In the event of prolonged storage, particularly at elevated temperature, systems such as these show a tendency towards coalescence of the oil droplets and phase separation. Accordingly, there is a continuing need to find emulsifiers which are capable of dispersing the oil phase very finely in the aqueous phase and which stabilize and emulsion for prolonged periods.

A review of McCutcheon's Emulsifiers & Detergents and Functional Materials (combined North American and International Editions) 1984 Annuals, MC Publishing Co., Glen Rock, N.J., U.S.A. (1984) indicates that several commercial products are available that contain palmitic and stearic acid derivatives, although the weight ratios of these components are not specified. Examples of such products are:

(a) "Tefose" 63 and 1500—a PEG (polyethylene glycol) palmito-stearate, nonionic base for O/W pharmaceutical ointments and lotions (a product of Gattefosse Corp., Hawthorne, N.Y., U.S.A);

(b) "Tefose" 2000—a PEG palmito-stearate with ethoxylated fatty alcohol, nonionic base for O/W cosmetic and pharmaceutical lotions having an HLB of 10.2;

(c) "Tefose" 2561—a glyceryl and PEG palmito-stearate with ethoxylated fatty alcohol, nonionic base for O/W pharmaceutical and cosmetic lotions and soft creams having an HLB of 10/11;

(d) "Cutina" MD-A—a mixture of mono- and diglycerides of palmitic and stearic acids, a nonionic consistency-giving agent for O/W and W/O systems (a product of Henkel Corporation, Ambler, Penna., U.S.A. and Henkel KGaA, Duesseldorf, F.R. Germany);

(e) glycerol stearate/palmitate, nonionic and anionic emulsifiers for food, cosmetics, and pharmaceuticals (products of Hefti, Ltd., Zurich, Switzerland);

(f) "Imwitor" glycerol monodiesters of palmitic/stearic acids, nonionic stabilizer dispersing agent for foods and cosmetics, and anionic O/W emulsifier for cosmetics and food when containing 8% potassium distearate (a product of Dynamit Nobel AG, Troisdorf, F.R. Germany); and (g) "Teginacid" ML blend of mono- and diglycerides of palmitic and stearic acid with PEG (40) stearate, emulsifier for finely dispersed emulsions (a product of Th. Goldschmidt AG, Essen, F.R. Germany).

There is no indication in the above publication that any of the above products use a critical weight ratio of palmitic to stearic acids.

SUMMARY OF THE INVENTION

It has now surprisingly been found that the weight ratio of palmitic acid-stearic acid mixtures has a significant effect on the emulsifying power of the soaps of such fatty acid mixtures and that soaps of a palmitic acid-stearic acid mixture of from 60 to 80% (preferably 70%) by weight palmitic acid and from 20 to 40% (preferably 30%) by weight stearic acid are particularly suitable for the preparation of O/W-emulsions, such percentages being equivalent to a palmitic:stearic weight ratio of 1:0.25–0.67, preferably 1:0.33–0.53, most preferably 1:0.43.

Accordingly, the present invention relates to an oil-in-water emulsifier, a method of emulsifying, and an emulsion comprising a continuous aqueous phase and a discontinuous oil phase and containing an emulsifier which comprises entirely or partly at least one soap of a palmitic acid-stearic acid mixture, in the above weight ratios.

BRIEF DESCRIPTION OF THE DRAWINGS

The three drawing figures are graphs showing that emulsions based on palmitic and stearic soap mixtures according to this invention.

have a significantly better, finer appearance (FIG. 1), show distinctly longer stability in storage at 50° C.

DETAILED DESCRIPTION OF THE INVENTION

Figure 1:
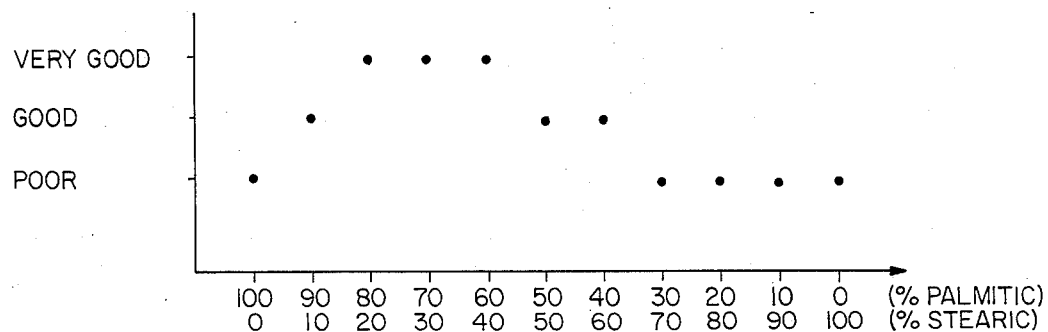

Other than in the operating examples, or where otherwise indicated, all members expressing quantities of ingredients or reaction conditions used herein are to be understood as modified in all instances by the term "about".

In one embodiment of this invention, an O/W emulsifier is afforded which consists essentially of a combination of a palmitic acid soap and a stearic acid soap, wherein the palmitic acid critically consists of 60% to 80%, preferably 70%, by weight, of the combined weight of the two acids. Other fatty acids may also be present in an amount not exceeding 10% of the combined weight of the acids, although they preferably are not present. Such other acids, are those that are normally associated with palmitic and/or stearic acids in technocal grade commercial mixtures, such as $C_{12-22}$ fatty acids including lauric, myristic, pentadecanoic, heptadecanoic, oleic, arachic, and/or behenic. Any suitable base may be used as the saponifying agent, provided that the resulting soap is suitable for an O/W emulsion. Preferred saponification bases are sodium (such as sodium carbonate and/or sodium hydroxide), potassium (such as potassium hydroxide), ammonium (such as aqueous ammonia), and/or an alkanolamine (such as a mono-, di-, or tri-($C_{2-4}$-alkanol)-amine), or mixtures of any of the foregoing.

In another embodiment of this invention, the above O/W emulsifier is formed in situ during the O/W emulsification process. In this instance, the palmitic acid and stearic acid, in the above weight ratios, are added to the oil phase. The base, which must be water-soluble, is added to the water phase. The two phases are then combined with sufficient mixing and sufficient heating, so as to at least partially saponify said acids and form an emulsion. At this point, sufficient of the palmitic-stearic acid mixture has been saponified to afford an emulsification-effective amount. Any unsaponified fatty acids remain in the oil phase of the emulsion and, in a preferred embodiment, a portion of the fatty acids is purposefully left unsaponified. The remaining unsaponified fatty acids should be enough to result in an emulsion pH of 4.5-8.5, preferably 6.5-7.5, most preferably 7.0, and become part of the oil phase.

A further embodiment of this invention is an emulsion containing an oil phase (O) and a water phase (W) in an O:W weight ratio of 1:1.5-9, preferably 1:3-8. As used herein, "oil phase" (O) means not only oil, but also all oil-soluble ingredients of the emulsion, such as the palmitic and stearic acid. Similarly, as used herein, "water phase" (W) means not only water, but also all water-soluble ingredients of the emulsion, such as the saponifying agents which will react with at least part of the palmitic and stearic acids in situ to form the emulsifier soap. The combined weight of palmitic and stearic acids, in the inventive weight ratios, will be 1-50% of the weight of the oil phase. The minimal amount of palmitic-stearic acids will be that which is enough to form an O/W emulsifying effective amount in situ with the saponifying agent (soap base) present. Similarly, enough saponifying agent must be present to saponify the palmitic-stearic acid mixture to an emulsification effective amount.

The oil phase is discontinuous and comprises cosmetic, food, or pharmaceutical oil components, fats and/or waxes, oil-soluble emulsifiers, including the palmitic acid-stearic acid soaps, and optionally oil-soluble pharmaceutical, food, or cosmetic active principles.

Suitable oil components are any of the known vegetable, animal, mineral and synthetic oils, for example (but not limited to) olive oil, sunflower oil, corn oil, whale oil, fish oil, mink oil, paraffin oil, silicone oils (such as dimethyl polysiloxane), squalene, oleyl alcohol, 2-octyl dodecanol, decyl oleate, isopropyl myristate, isononyl stearate, 2-ethylhexyl palmitate, glycerol tricaprylate and other esters, and alcohols or hydrocarbons known as cosmetic oil components.

Suitable cosmetic fats and waxes are any known products having melting points of up to approximately 80° C., for example (but not limited to): hardened vegetable and animal fats (triglycerides); spermaceti; fatty alcohols, for example cetyl alcohol, stearyl alcohol; esters such as cetyl palmitate; natural waxes such as wool wax, beeswax, japan wax, carnauba wax, candelilla wax; mineral waxes such as montan wax, paraffins, Vaseline; and synthetic paraffins such as the polyethylene waxes. Also included are the optionally present non-saponified fractions of the palmitic acid-stearic acid mixture. These waxes generally make up no more than about 50% by weight of the oil phase. At least one soap of the palmitic acid-stearic acid mixture is preferably used as the only emulsifier. However, other known oil-soluble O/W-emulsifiers may also be used in small amounts of up to 25% by weight of the total oil phase.

Suitable oil-soluble emulsifiers which may be additionally present include any of the oil-soluble emulsifiers suitable for emulsifying the abovementioned oils, fats and waxes, such as at least one of: the soaps of $C_{12-15}$ or $C_{20-22}$ fatty acids; the mono- and diglycerides and the sorbitan partial esters of $C_{12-22}$ fatty acids; the adducts of from 2 to 30 mols ethylene oxide with such fatty acid partial glycerides and sorbitan fatty acid esters; the adducts of from 2 to 30 mols ethylene oxide with $C_{12-22}$-fatty alcohols, with $C_{12-22}$-fatty acids, with $C_{8-16}$-alkyl) phenols, and with $C_{16-22}$-fatty acid alkanolamides; $C_{16-22}$-fatty alcohol sulfates in the form of their alkali or ($C_{1-6}$) alkanolammonium salts; or phosphoric acid esters of linear $C_{16-22}$-fatty alcohols or of $C_{16-22}$-fatty alcohol polyglycol ethers in the form of their alkali or ($C_{1-6}$) alkanolammonium salts.

In addition to the constituents mentioned, the discontinuous oil phase may also contain at least one oil-soluble active component, for example: light stabilizers; anti-oxidants; vitamins; oil-soluble preservatives, such as a p-hydroxybenzoic acid benzyl ester; or food or pharmaceutically active compounds.

In the most simple case, the continuous aqueous phase of the O/W-emulsions according to this invention may consist essentially of water and at least one alkalizing agent (for example potassium hydroxide and/or triethanolamine). However, auxiliaries which favorably affect the stability and performance properties of the O/W-emulsions are preferably added to the aqueous phase.

In the case of cosmetic O/W-emulsions intended for skin-care and/or hair-care purposes, it is advisable to add to the aqueous phase for cold stabilization from 1 to 30% by weight, based on the aqueous phase, of at least one glycol or polyol selected from the group comprising propylene glycol, polyethylene glycol, hexylene glycol, glycerol and sorbitol and from 0.05 to 3.0% by weight, based on the aqueous phase, of at least one water-soluble polymer selected from the group comprising water-soluble polysaccharides, water-soluble polysaccharide ethers, acrylic acid polymers and copolymers, polyvinyl alcohol and polyvinyl pyrrolidone.

It is of particular advantage to add a combination of (a) a water-soluble nonionic cellulose ether and (b) a cross-linked acrylic acid polymer or copolymer having an average molecular weight of from 1,000,000 to 5,000,000 in the form of a water-soluble salt in a quantitative ratio (a):(b) of 1:0.11–9. This combination of hydrocolloids has a favorable multiplier effect and increases the viscosity of the aqueous phase so that the O/W-emulsions obtained in this way show more "body" when applied to the skin.

Suitable crosslinked acrylic acid polymers are products obtained by copolymerization of acrylic acid with from 0.1 to 4.0% by weight of a poly-$C_{2-5}$-alkenyl polyether of a polyhydric alcohol containing more than one alkylene ether group in the molecule as crosslinking agent. One example of such a crosslinking agent is polyallyl sucrose.

Other comonomers may also be used in the production of the crosslinked acrylic acid polymers in quantities of up to 59% by weight of the monomer mixture. Suitable comonomers are, for example, maleic acid anhydride, N-methyl acrylamide, methylvinylether or mixtures of these additional monomers. Crosslinked acrylic acid polymers such as these are known from U.S. Pat. No. 2,798,053 incorporated herein by reference, and are commercially available under the trademark "CARBOPOL" from B. F. Goodrich Chem. Co., Cleveland, Ohio, U.S.A. The crosslinked acrylic acid polymers may be dispersed in water, although the strong thickening effect is only achieved when the polymers are converted into the salt form by inorganic bases such as sodium hydroxide, potassium hydroxide, or ammonia, or by low molecular weight amines or alkanolamines.

In addition to the glycols or polyols and water-soluble polymers mentioned, the continuous aqueous phase may contain other water-soluble auxiliaries, including water-soluble salts, such as buffers, for example alkali phosphate, alkali citrate, borates; water-soluble preservatives, for example, p-hydroxybenzoic acid methyl ester, sorbic acid; water-soluble surfactants or emulsifiers; water-soluble dyes; or water-soluble cosmetic or pharmaceutical active components, for example water-soluble vegetable extracts, water-soluble proteins or protein derivatives, amino acids, etc.

The palmitic-stearic soaps useful in this invention may be prepared by separate saponification of palmitic acid and stearic acid followed by simple mixing in the inventive weight ratios. It also is possible to mix the acids in the inventive weight ratios and saponify them simultaneously. In a preferred embodiment, the palmitic and stearic acids are prepared in situ during the emulsification itself, by mixing the acids, saponifiers, oil, water, and other ingredients, simultaneously.

The O/W-emulsion is preferably prepared as follows:

The oil components, fats, and optional waxes are mixed with the inventive proportions of a palmitic acid-stearic acid mixture and optional other oil-soluble emulsifiers and oil-soluble active components and the resulting mixture heated until a homogenous melt is formed. The components of the aqueous phase, i.e. the water, the glycols or polyols preferably present, the water-soluble polymers, the other water-soluble auxiliaries present, if any, and the quantity of base required for the desired degree of saponification of the palmitic acid-stearic acid mixture, such as sodium hydroxide, potassium hydroxide, ammonia solution or an alkanolamine, for example, triethanolamine, are dissolved in water and preferably heated to around 70° to 90° C. The oil phase and the aqueous phase are then mixed together with intensive stirring and stirred for at least 5 minutes at 70° to 90° C. until a pH of 4.5 to 8.5 is reached, preferably until neutralization. The emulsion thus formed is then cooled to room temperature.

The emulsions according to the invention are distinguished by particular fineness and stability and also by a viscosity which is considerably higher than that of emulsions of otherwise the same composition prepared with soaps of palmitic acid, of stearic acid, or of a palmitic acid-stearic acid mixture containing less than 60% by weight palmitic acid or less than 20% by weight stearic acid.

The following Examples further illustrate the invention.

EXAMPLES

Skin Emulsions

| Ingredient (% by weight) | Example 1 | Example 2 | Example 3 |
|---|---|---|---|
| Paraffin oil, thinly liquid (paraffinum perliquidum DAB) | 15 | 12 | 10 |
| Isopropyl palmitate | — | 3 | 5 |
| Palmitic acid-stearic acid mixture (70% by weight $C_{16}$, 30% by weight $C_{18}$) | 0.5 | 0.5 | 0.5 |
| Propylene glycol | 3 | 3 | 3 |
| Triethanolamine | 0.2 | 0.2 | 0.2 |
| p-Hydroxybenzoic acid methylester | 0.2 | 0.2 | 0.2 |
| p-Hydroxybenzoic acid propylester | 0.1 | 0.1 | 0.1 |
| Carboxyvinyl polymer ("Carbopol" 940) | 0.1 | 0.15 | 0.15 |
| Water (q.s. to 100%) | | | |

The skin emulsion of Example 1 was prepared for otherwise the same composition with palmitic acid-stearic acid mixtures of which the $C_{16}/C_{18}$ ratio by weight was varied from 100/0 to 0/100 in 10% intervals.

O/W-emulsions were obtained in every case, but differed in their appearance (fineness), stability in storage at 50° C. and viscosity.

Figure 2:
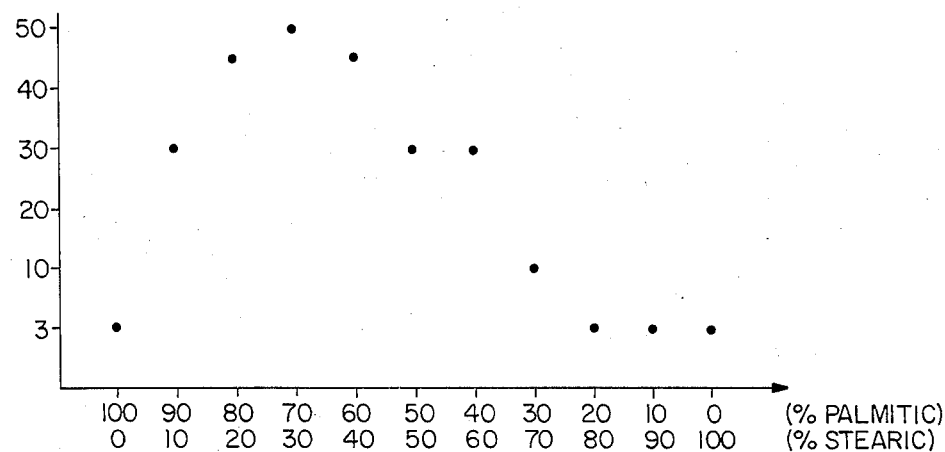
(FIG. 2) and have a higher viscosity (FIG. 3).
Figure 3:
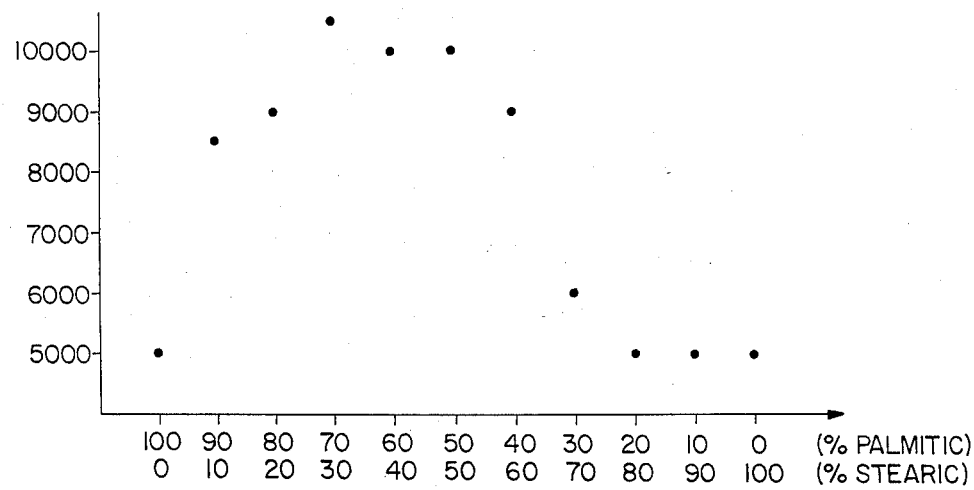

The results of the 11 variations of Example 1 were tested for the above qualities and the results plotted in FIGS. 1–3 according to the following.

FIG. 1: Appearance was assessed immediately after preparation on the basis of the following criteria: very good: very fine, white emulsion good: less fine, white emulsion poor: coarse droplets, opaque emulsion FIG. 2: The samples were stored in sealed vessels at 50° C. in a thermostat until clearly visible inhomogeneity or separation occurred.

FIG. 3: Viscosity was measured 48 hours after preparation at 20° C. using a Brookfield rotational viscosimeter (spindle 5, 10 r.p.m.)

A study of the Figures indicates that very good optical appearance (indicating the emulsification quality) was only obtained at 60–80% by weight palmitic. Similarly, a noticeably higher stability was only evidenced at 60–80% (optimum at 70%) by weight palmitic. Although an acceptable viscosity was achieved at 40–80% by weight palmitic, the optimum was at 70% by weight, and it is only within the range 60–80% palmitic (the balance q.s. to 100% being stearic) that all three factors were optimized, with about 70% by weight being most optimal.

Further Application Examples:

4. Skin-care cream, O/W
| "Cutina" MD[1] | 5.0% by weight |
| 2-Octyldodecanol | 4.0 by weight |
| Paraffin oil, thinly liquid | 4.0 by weight |
| Palmitic-stearic acid (70:30) | 3.0 by weight |

| | |
|---|---|
| Cetylalcohol | 2.0 by weight |
| Glycerol, 86% by weight | 3.0 by weight |
| Potassium hydroxide | 0.25 by weight |
| "Carbopol" 934[9] | 0.2 by weight |
| Water | q.s. to 100.0 by weight |
| 5. Night Cream, O/W | |
| Palmitic-stearic acid (70:30) | 6.0% by weight |
| "Cutina" MD[1] | 5.0% by weight |
| Cetylalcohol | 1.0 by weight |
| "Eumulgin" B1[2] | 1.0 by weight |
| 2-Octyldodecanol | 8.0 by weight |
| "Myritol" 318[4] | 3.0 by weight |
| Paraffin oil, thinly liquid | 3.0 by weight |
| "Hydagen" F[5] | 0.2 by weight |
| "Carbopol" 940[8] | 0.4 by weight |
| Triethanolamine | 1.5 by weight |
| Water | q.s. to 100.0 by weight |
| 6. Moisturizing emulsion, O/W | |
| Palmitic-stearic acid (70:30) | 4.0% by weight |
| Cetyl-stearyl alcohol | 2.0 by weight |
| "Eumulgin" B2[3] | 2.0 by weight |
| Isopropyl myristate | 5.0 by weight |
| 2-Octyldodecanol | 2.0 by weight |
| "Myritol" 318[4] | 3.0 by weight |
| Sorbitol, 70% | 3.0 by weight |
| "Carbopol" 941[10] | 0.7 by weight |
| "Viscontran" MHPC 3000[6] | 0.6 by weight |
| Triethanolamine | 1.5 by weight |
| Water | q.s. to 100.0 by weight |
| 7. Skin-care milk, O/W | |
| Palmitic-stearic acid (70:30) | 2.5% by weight |
| Paraffin oil, thinly liquid | 4.0 by weight |
| "Hostaphat" KW 340 N[7] | 2.0 by weight |
| 2-Octyldodecanol | 8.0 by weight |
| Cetyl-stearyl alcohol | 1.0 by weight |
| Glycerol, 99.5% | 5.0 by weight |
| Triethanolamine | 0.9 by weight |
| Vegetable extracts, aqueous | 10.0 by weight |
| "Carbopol" 940[8] | 0.2 by weight |
| "Viscontran" MHPC 3000[6] | 0.3 by weight |
| Water | q.s. to 100.0 by weight |

The following trademarked products were used in formulations 4 to 7:
(1) "Cutina" MD: a mixture of mono- and diglycerides of palmitic and stearic acid (Henkel KGaA, Duesseldorf, F.R. Germany)
(2) "Eumulgin" B1: cetyl-stearyl alcohol+12 mols ethylene oxide (Henkel KGaA)
(3) "Eumulgin" B2: cetyl-stearyl alcohol+20 mols ethylene oxide (Henkel KGaA)
(4) "Myritol" 318: caprylic-capric acid triglyceride (Henkel KGaA)
(5) "Hydagen" F: sodium salt of a polyhydroxycarboxylic acid (Henkel KGaA)
(6) "Viscontran" MHPC 3000: methylhydroxypropyl cellulose, viscosity 2% in distilled water (20° C., Brookfield viscosimeter, 20 r.p.m.) 2900-4400 mPas (Henkel KGaA)
(7) "Hostaphat" KW 340N: phosphoric acid ester of a wax alcohol+4 mols ethylene oxide adduct (Hoechst AG, Frankfut am Main, F.R. Germany)
(8) "Carbopol" 940: crosslinked acrylic acid polymer, average molecular weight ca. 4,000,000 (B. F. Goodrich Chemical Co., Cleveland, Ohio, U.S.A.)
(9) "Carbopol" 934: crosslinked acrylic acid polymer, average molecular weight ca. 3,000,000 (B. F. Goodrich Chem. Co.)
(10) "Carbopol" 941: crosslinked acrylic acid polymer, average molecular weight ca. 1,250,000 (B. F. Goodrich Chem. Co.)

I claim:

1. In an oil-in-water emulsion comprising: a discontinuous oil and oil-soluble-component phase (O); a continuous water and water-soluble-component phase (W) in an O:W weight ratio of about 1:1.5–9; and at least one emulsifier; the improvement of employing as one said emulsifier an emulsifier-effective amount of a combination of at least one palmitic acid soap and at least one stearic acid soap in a palmitic:stearic weight ratio of about 1:0.25–0.67, wherein the saponification base for each said palmitic acid soap and each said stearic acid soap is at least one of: sodium, potassium, ammonium, mono ($C_{2-4}$-alkanol) amine, di($C_{2-4}$-alkanol)amine, or tri($C_{2-4}$-alkanol) amine.

2. The emulsion of claim 1 wherein said palmitic:stearic weight ratio is about 1:0.33–0.53.

3. The emulsion of claim 2 wherein said water-soluble-component consists essentially of: propylene glycol, polyethylene glycol, hexylene glycol, glycerol, sorbitol, or a mixture thereof, present in about 1–30% by weight; and/or a polysaccharide, polysaccharide ether, acrylic acid polymer or copolymer which may be crosslinked, polyvinyl alcohol, polyvinyl pyrrolidone, or a mixture thereof, present in about 0.05–3% by weight; all percentages based upon the weight of the water and water-soluble-component phase.

4. The emulsion of claim 1 wherein said palmitic-stearic weight ratio is about 1:0.43.

5. The emulsion of claim 1 wherein the saponification base for said soaps is triethanolamine.

6. The emulsion of claim 1 wherein said at least one emulsifier is present in about 1–50% by weight, based upon the weight of said oil and oil-soluble-components phase.

7. The emulsion of claim 1 wherein said emulsifier is formed in situ by the saponification of at least part of said palmitic and stearic acids with at least one saponification base, the amount of formed emulsifier being determined by saponifying until said emulsion has a pH of about 4.5–8.5.

8. The emulsion of claim 7 wherein said palmitic and stearic acids are only partially saponified and wherein the unsaponified acids are oil-soluble-components.

9. The emulsion of claim 8 wherein said water-soluble-component consists essentially of: propylene glycol, polyethylene glycol, hexylene glycol, glycerol, sorbitol, or a mixture thereof, present in about 1–30% by weight; and/or a polysaccharide, polysaccharide ether, acrylic acid polymer or copolymer which may be crosslinked, polyvinyl alcohol, polyvinyl pyrrolidone, or a mixture thereof, present in about 0.05–3% by weight; all percentages based upon the weight of the water and water-soluble-component phase.

10. The emulsion of claim 1 wherein said water-soluble-component consists essentially of at least one glycol, polyol, polymer, or copolymer.

11. The emulsion of claim 1 wherein said water-soluble-component consists essentially of: propylene glycol, polyethylene glycol, hexylene glycol, glycerol, sorbitol, or a mixture thereof, present in about 1–30% by weight; and/or a polysaccharide, polysaccharide ether, acrylic acid polymer or copolymer which may be crosslinked, polyvinyl alcohol, polyvinyl pyrrolidone, or a mixture thereof, present in about 0.05–3% by weight; all percentages based upon the weight of the water and water-soluble-component phase.

12. A method for preparing an oil-in-water emulsion comprising a discontinuous oil and oil-soluble-components phase (O), a continuous water and water-soluble-components phase (W) in an O:W weight ratio of about 1:1.5–9, and an emulsifier-effective amount of at least one emulsifier consisting essentially of a palmitic acid soap and a stearic acid soap in a palmitic:stearic ratio of about 1:0.25–0.67, wherein said soaps are formed in situ during the emulsion formation by (a) including said palmitic acid and said stearic acid in said oil soluble-components, (b) including at least one water-soluble saponification base comprising sodium, potassium, ammonium, mono($C_2$–$C_4$-alkanol) amine, di($C_2$–$C_4$-alkanol) amine, or tri($C_2$–$C_4$-alkanol)amine, in said water-soluble components, (c) combining said oil phase and said water phase accompanied by mixing and heating to effect saponification of said acids, and (d) continuing said saponification until an emulsion is formed having a pH of about 4.5–8.5.

13. The method of claim 12 wherein: said palmitic acid and said stearic acid are added to said oil-soluble-components in a palmitic:stearic ratio of about 1:0.43; and the saponification of said acids is only partial, the unsaponified acids remaining in the discontinuous oil phase of said emulsion.

14. The method claim 13 wherein said saponification is continued until said emulsion has a pH of about 6.5–7.5.

15. The method claim 12 wherein said saponification is continued until said emulsion has a pH of about 6.5–7.5.

* * * * *